United States Patent [19]
Blenke et al.

[11] Patent Number: 6,049,023
[45] Date of Patent: Apr. 11, 2000

[54] EXTENSIBLE ABSORBENT ARTICLE INCLUDING A TEARABLE LAYER

[75] Inventors: Timothy James Blenke, Neenah; Jennifer Elizabeth Pozniak, Appleton, both of Wis.

[73] Assignee: Kimberly-Clark Worldwide, Inc., Neenah, Wis.

[21] Appl. No.: 09/001,347

[22] Filed: Dec. 31, 1997

[51] Int. Cl.[7] .................................................. A61F 13/15
[52] U.S. Cl. .......................... 604/365; 604/358; 604/367; 604/385.1; 604/374; 604/375; 604/368
[58] Field of Search .................................... 604/369, 373, 604/385.2, 367, 368, 378, 385.1, 365, 358, 374, 375

[56] References Cited

U.S. PATENT DOCUMENTS

| | | | |
|---|---|---|---|
| 3,653,382 | 4/1972 | Easley et al. | 128/284 |
| 3,769,978 | 11/1973 | DeNight et al. | 128/287 |
| 4,353,762 | 10/1982 | Bouda | 156/164 |
| 4,573,987 | 3/1986 | Lamb, Jr. | 604/378 |
| 4,655,760 | 4/1987 | Morman et al. | 604/385 A |
| 4,959,059 | 9/1990 | Eilender et al. | 604/358 |
| 5,226,992 | 7/1993 | Morman | 156/62.4 |
| 5,330,598 | 7/1994 | Erdman et al. | 156/164 |
| 5,702,378 | 12/1997 | Widlund et al. | 604/373 |
| 5,800,419 | 9/1998 | Soga et al. | 604/368 |
| 5,824,004 | 8/1998 | Osborn, III et al. | 604/385.2 |
| 5,827,259 | 8/1998 | Laux et al. | 604/385.2 |
| 5,833,677 | 11/1998 | Sauer | 604/369 |
| 5,843,056 | 12/1998 | Good et al. | 604/367 |

FOREIGN PATENT DOCUMENTS

| | | | |
|---|---|---|---|
| 0 591 647 A2 | 4/1994 | European Pat. Off. | A61F 13/15 |
| WO 93/01786 | 2/1993 | WIPO | A61F 13/15 |
| WO 96/19349 | 6/1996 | WIPO | B32B 27/12 |

*Primary Examiner*—John G. Weiss
*Assistant Examiner*—Miley Craig Peppers, III
*Attorney, Agent, or Firm*—Thomas D. Wilhelm

[57] ABSTRACT

An absorbent article includes an absorbent pad and an outer cover. The absorbent pad includes an absorbent core enveloped by a first layer and a second barrier layer. The first layer and the second barrier layer are secured to each other outwardly of a perimeter of the absorbent core. A deformable third layer is disposed in the absorbent article between the first layer and an outer cover. The deformable layer is adhesively secured to the inner surface of the outer cover. There is no significant securement between the deformable layer and the first layer. In embodiments where the outer cover is extensible in a cross-direction and/or a longitudinal direction, the deformable layer deforms during extension of the outer cover, but such deforming has no significant harmful effect on the first layer. Therefore, damage to the first layer, the second barrier layer, or the absorbent pad, and concomitant release of superabsorbent material from the absorbent pad, is avoided.

39 Claims, 3 Drawing Sheets

EXTENSIBLE ABSORBENT ARTICLE INCLUDING A TEARABLE LAYER

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Absorbent articles such as infant diapers, training pants, adult incontinence products, and the like are well known. Such absorbent articles have achieved wide acceptance due to their ability to receive and absorb body exudates, whether large amounts or small, and generally include an absorbent core therein.

In typical absorbent articles, an absorbent pad has an absorbent core contained within a barrier tissue and a forming tissue. The absorbent pad is located between an outer cover and a bodyside liner.

This invention pertains to improvements in extensible absorbent articles for use in receiving and storing exudates.

BACKGROUND OF THE INVENTION

In general, absorbent articles should comfortably fit the body of a wearer. Most absorbent articles include an absorbent pad having an absorbent core contained in a wrap comprising a barrier tissue and/or a forming tissue.

In conventional structures, the outer cover is typically adhesively secured to the forming tissue of the absorbent pad. In such embodiments, extending an extensible outer cover in the cross-direction extends the forming tissue in the cross-direction. The force used to extend the outer cover, and thence the absorbent pad, can tear or otherwise damage the forming tissue or the barrier tissue of the absorbent pad. Since the absorbent pad is typically a sealed enclosure, namely an absorbent core enclosed within the combination of a forming tissue and a barrier tissue, tearing the absorbent pad, namely either the forming tissue or the barrier tissue, can release superabsorbent particles and other absorbent materials from the absorbent pad, which absorbent materials may then come into contact with the body of the wearer. Such materials can irritate the skin of the wearer, and such release indicates failure of the absorbent article to perform properly. Therefore, it is highly desirable to find a way to prevent tearing or other structural failure of the absorbent pad in absorbent articles which use an extensible outer cover and/or an extensible bodyside liner.

SUMMARY OF THE DISCLOSURE

In the present invention, an absorbent article comprises an absorbent core having a first side and a second side, a first layer of material disposed adjacent the first side of the absorbent core, a second deformable layer of material disposed in surface-to-surface relationship with the first layer, an extensible outer cover disposed in surface-to-surface relationship with the second layer, and adhesive disposed between the second layer and the outer cover, the adhesive securing the second layer to the outer cover such that the second layer can tear during extension of the outer cover with no harmful effect on the first layer of material, the first layer of material assisting in retaining superabsorbent material of the absorbent core.

In many embodiments, tearing of the second layer creates no significant loading on the first layer of material. The second layer effectively shields the first layer from adhering action of the adhesive.

In some embodiments, the first layer and/or the second layer are tissues.

In many embodiments, the second layer has a second width at least as great as the first layer.

In some embodiments, the second layer overlies the entirety of the first layer.

In some embodiments a third barrier layer is disposed adjacent the second side of the absorbent core, the third barrier layer and the first layer, in combination, containing the absorbent core. In such embodiments, the absorbent core, the first layer, and the third barrier layer, in combination, generally define the absorbent pad.

In some embodiments, the first layer and the third barrier layer are adhesively secured to each other outwardly of an outer perimeter of the absorbent core.

In some embodiments, a bodyside liner is disposed in surface-to-surface relationship with the third barrier layer.

In some embodiments, at least one of the bodyside liner and the outer cover comprises a resiliently extensible material.

In some embodiments, both the bodyside liner and the outer cover are resiliently extensible, and have substantially equal resilient extensibilities in each of the longitudinal direction and the cross direction.

In some embodiments, the bodyside liner and the outer cover are both extensible in at least the cross-direction.

In some embodiments, the outer cover comprises a neck bonded laminate.

In some embodiments, the absorbent article includes first and second containment flaps.

In some embodiments, the absorbent article is devoid of separate waist elastic elements, and is resiliently stretchable in the waist.

In some embodiments, the absorbent article includes leg elastics disposed at least in the crotch portion, the leg elastics providing extensibility and retractability, of the absorbent article, in the longitudinal direction.

In some embodiments, the adhesive comprises a pattern having an array of swirls.

In some embodiments, the absorbent article is effectively free from adhesive bonding between the first and second layers.

In some embodiments, the bodyside liner comprises an extensible material.

In some embodiments, the bodyside liner and outer cover are extensible in at least the cross-direction, the second layer being designed to tear or stretch, thus enabling the outer cover to extend at least about 30 percent in the cross-direction without damaging the first layer or the absorbent pad. In other embodiments, tearing of the tearable layer which is adhered to the outer cover enables the outer cover to extend at least about 200 percent in the cross-direction without damaging the first layer, which is between the absorbent core and the tearable layer, or otherwise damaging the absorbent pad.

In some embodiments, tearing of the tearable layer enables the outer cover to extend at least about 30 percent in the longitudinal direction without damaging the first layer or otherwise damaging the absorbent pad.

The invention is not limited in its application to the details of construction and the arrangements of components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in absorbent articles, but it should be understood that potential uses of the structures of the present invention need not be limited to the context of absorbent articles.

As used herein and in the claims that follow, the phrase "absorbent article" is meant to include diapers, training pants, adult incontinence articles, feminine hygiene products, and the like. Such articles generally receive and/or store urine and/or fecal material, or have a significant other absorbent function.

Figure 1:
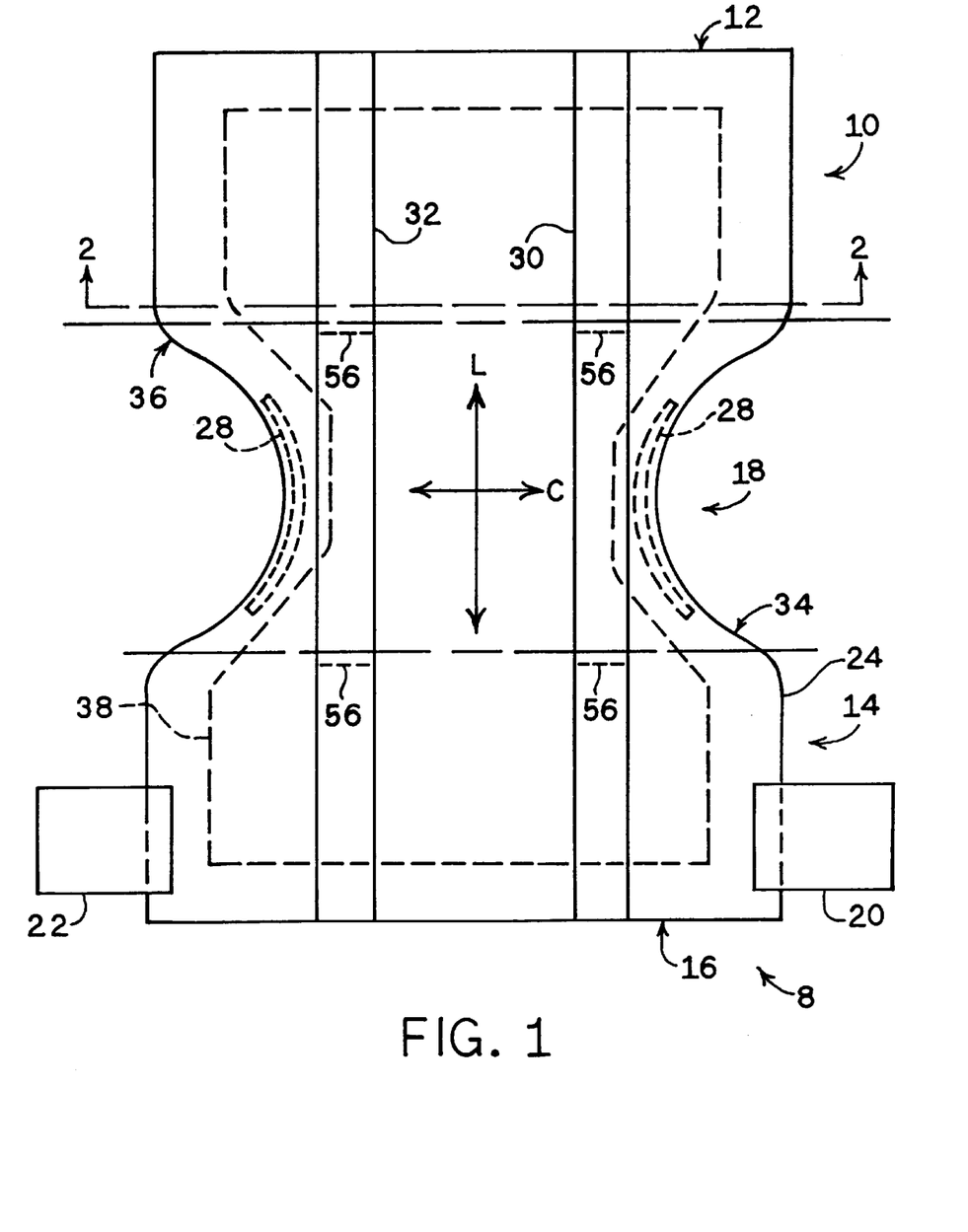
FIG. 1 shows a top view of a first embodiment of an absorbent article of the invention.

FIG. 1 is a representative top view of an absorbent article 8 of one embodiment of the present invention, in its uncontracted state (i.e. with all elastic-induced gathering and contraction removed). Absorbent article 8, shown in FIG. 1, includes a front portion 10 having a front edge 12, a rear portion 14 having a rear edge 16, and a crotch portion 18 between the front portion and the rear portion. Fastening tabs 20, 22 are secured to and extend outwardly from opposing sides of bodyside liner 24 in rear portion 14. Extensible outer cover 26 (shown in FIG. 2) lies in surface-to-surface relationship with bodyside liner 24 about outer perimeter of respective such layers. Leg elastics 28 provide generally longitudinally retractable extensibility and support in crotch portion 18. Containment flaps 30, 32 extend longitudinally along the length of absorbent article 8 inwardly of respective side edges 34, 36 of the absorbent article. Containment flaps 30, 32 are typically secured to bodyside liner 24. Absorbent pad 38 (shown in FIG. 2) may have an hour-glass shape and is disposed between bodyside liner 24 and outer cover 26.

Figure 2:
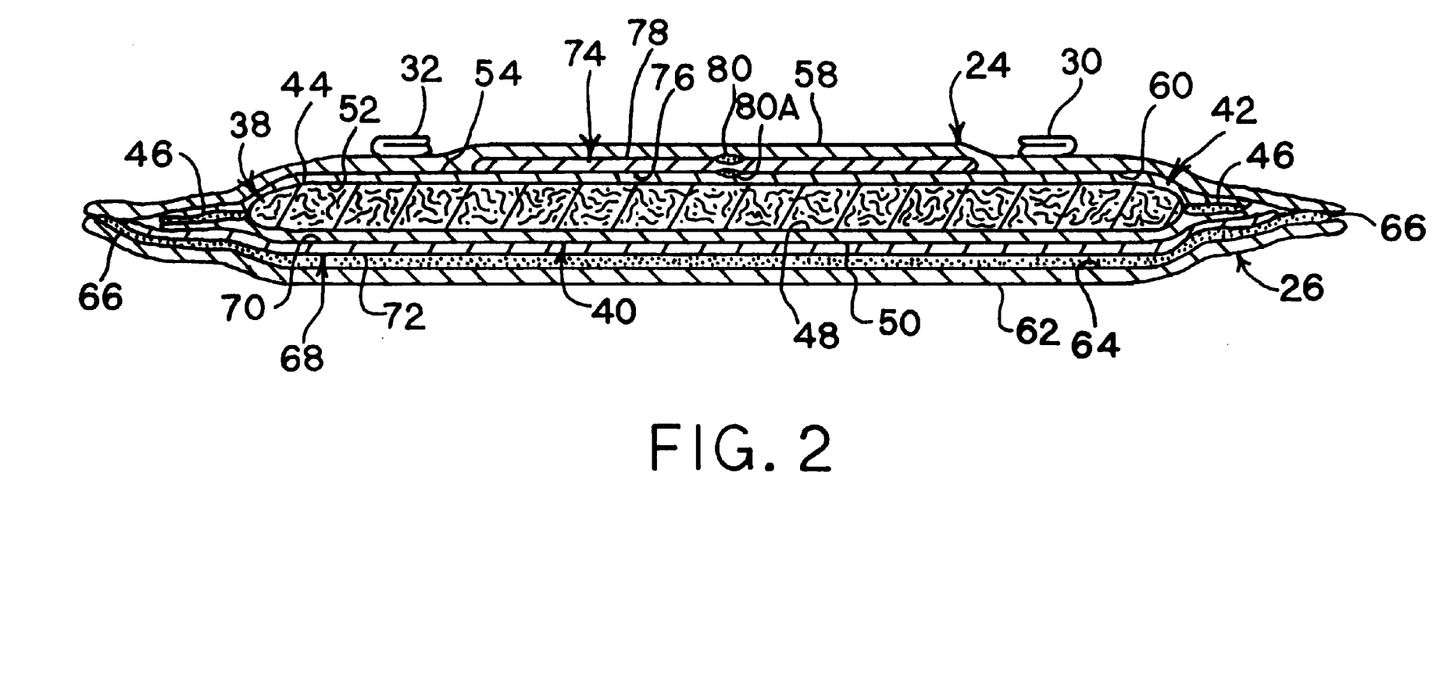
FIG. 2 shows a cross section view of the absorbent article taken at 2—2 of FIG. 1.

In FIG. 2, absorbent pad 38 is located between bodyside liner 24 and outer cover 26. Absorbent pad 38 includes a first layer 40 and a second barrier layer 42, in combination, surrounding an absorbent core 44. First layer 40 typically is disposed adjacent a first side of absorbent core 44 and second layer 42 typically is disposed adjacent a second opposing side of the absorbent core. Adhesive 46 secures first layer 40 and second barrier layer 42 to each other. Adhesive 46 can be disposed over e.g. the entirety of any one of layer 40, layer 42, or absorbent core 44. Thus first layer 40 and second barrier layer 42 envelope absorbent core 44 and thereby form absorbent pad 38. First layer 40 includes a first inner surface 48 and a second opposing outer surface 50. Likewise, second barrier layer 42 includes a first inner surface 52 and a second opposing outer surface 54. Absorbent pad 38 receives and retains exudates that pass through bodyside liner 24. Adhesive 46 secures a portion of first surface 48 of first layer 40 to a portion of first surface 52 of second barrier layer 42 about an outer perimeter of absorbent core 44.

Bodyside liner 24 has a first skin-facing surface 58 and a second opposing surface 60. Outer cover 26 includes a first outer surface 62 and a second opposing inner surface 64. A layer of adhesive 66 is disposed on second inner surface 64 of outer cover 26 and thus secures the outer cover to second surface 60 of bodyside liner 24 outwardly of the perimeter of absorbent pad 38.

A third layer 68 is disposed between a portion of second inner surface 64 of outer cover 26 and second surface 50 of first layer 40. Third layer 68 includes a first surface 70 in surface-to-surface relationship with second surface 50 of first layer 40, and a second surface 72 in surface-to-surface relationship with inner surface 64 of outer cover 26.

Figure 3:
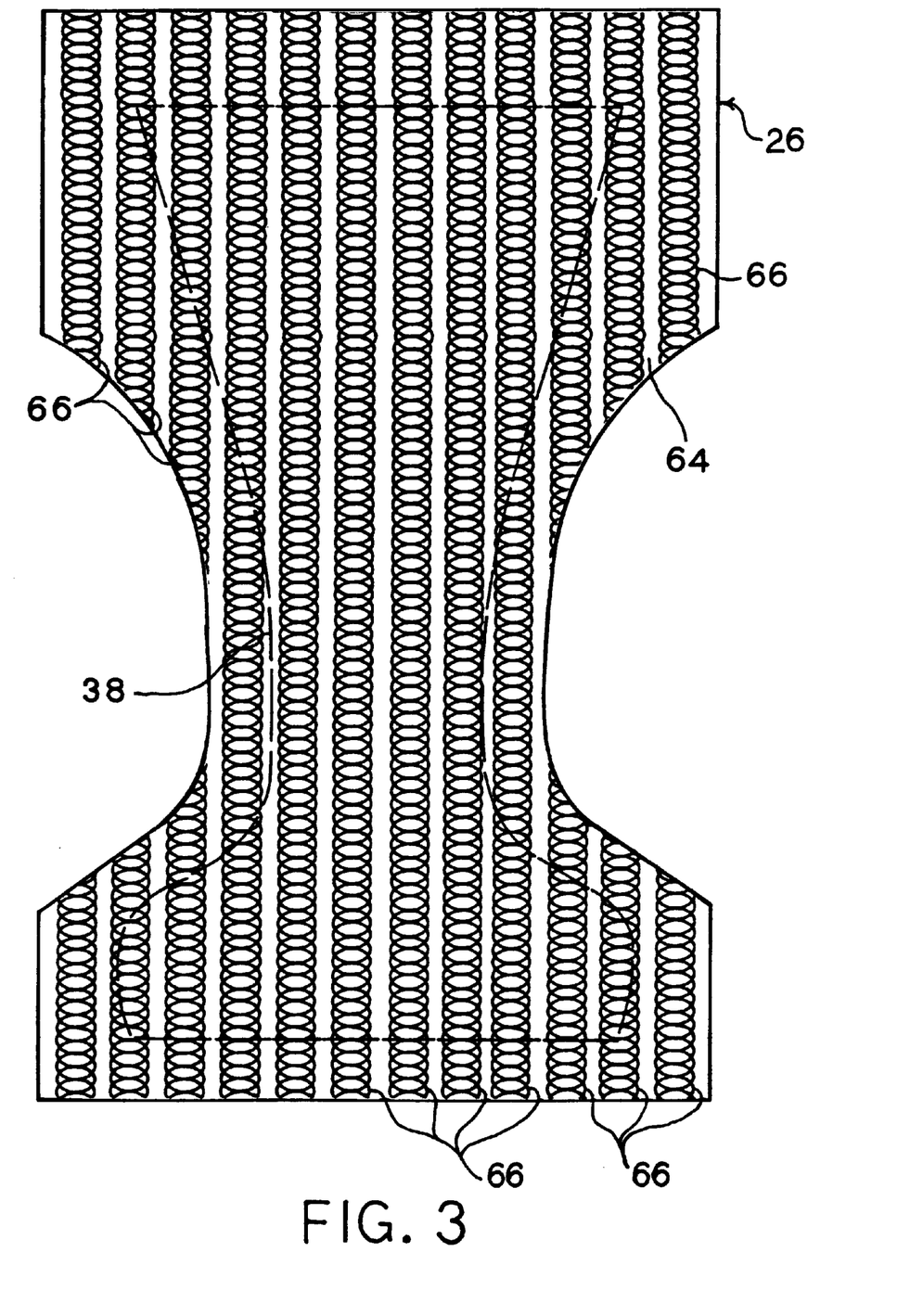
FIG. 3 shows an inner surface of an outer cover, having adhesive applied to the inner surface in a preferred adhesive pattern.

As shown in FIG. 3, a pattern of adhesive 66 covers substantially the entire second inner surface 64 of outer cover 26. Pattern of adhesive 66 secures third layer 68 to outer cover 26.

Adhesive 66 does not migrate through third layer 68. Accordingly, absorbent pad 38 is effectively free from adhesive bonding between second surface 50 of first layer 40 and first surface 70 of third layer 68 over the portion of the first layer. Thus, during extension of outer cover 26, third layer 68 can deform, for example tear or stretch, with no significant harmful effect on first layer 40 or absorbent pad 38. Therefore, superabsorbent material in absorbent pad 38 does not escape past first layer 40, despite the expected, and planned for, damage to third layer 68.

In preferred embodiments of the invention, outer cover 26 and bodyside liner 24 are extensible elements. Preferably at least one of the elements is resiliently extensible. Outer cover 26 preferably is extensible at least in cross-direction "C".

In prior art structures, extension of the outer cover, if firmly secured to the absorbent pad over substantially the entirety of a layer corresponding to the first layer, applies force to the first layer and thus to the absorbent pad. Such force may cause the first layer, and/or a second layer on the opposing side of the absorbent core, to tear and thus release superabsorbent material from the absorbent pad. Such release of superabsorbent material, and concomitant superabsorbent material reaching the skin of a wearer, can cause discomfort to the wearer, and is considered product failure.

However, in the instant invention, third layer 68 is disposed between first layer 40 and outer cover 26. Third layer 68, secured to outer cover 26 by adhesive 66, typically tears or stretches during extension of the outer cover, but such tearing has no significant harmful effect on absorbent pad 38 since layer 68 is not a containment layer with respect to absorbent core 44 or any other element of absorbent pad 38.

FIG. 2 also illustrates surge layer 74 having a first surface 76 and a second opposing surface 78. First surge layer surface 76 is disposed in surface-to-surface relationship with second surface 54 of second layer 42. Since generally no adhesive is directly applied between bodyside liner 24 and absorbent pad 38, the bodyside liner has relatively free mobility with respect to the absorbent pad.

A line of adhesive 80 disposed in the longitudinal direction "L" extends along the center of bodyside liner 24. Adhesive 80 thus secures bodyside liner 24 to second surface 78 of surge layer 74 along a longitudinal centerline, thereby securing surge layer 74 to bodyside liner 24 at a proper location for use of the surge layer in absorbent article 8. Having a single longitudinal line of adhesive 80 allows bodyside liner 24 freedom to extend outwardly in the cross-direction "C" without significant resistance from surge layer 74 whereby the integrity of the surge layer is typically not threatened by such extension. Since surge layer 74 is secured to bodyside liner 24 but not to layer 42, and thus not to absorbent pad 38, the surge layer is relatively free to move with respect to absorbent pad 38.

In embodiments wherein bodyside liner 24 is extensible in longitudinal direction "L", adhesive 80 can comprise a line, pattern, or array of adhesive in cross direction "C" (not shown). Such line, pattern or array of adhesive can be applied by a printing roll or other known methods. Such line, pattern or array of adhesive 80, enables bodyside liner 24 to extend in longitudinal direction "L" despite concomitant securement of bodyside liner 24 to surge layer 74.

Adhesive 80 preferably comprises a hot melt adhesive. Other known types of adhesives can also be utilized as adhesive 80.

Fastening tabs 20, 22 can comprise hooks of a hook and loop fastener system for securing rear portion 14 of absorbent article 8 to front portion 10 when the absorbent article is mounted or a wearer. Other well known securing elements can be used to support absorbent article 8 on the wearer. For example, a cohesive system, an adhesive fastener system, or the like, may be utilized as securing elements, with suitable cooperating elements on front portion 10, as necessary, to support absorbent article 8 on the wearer. One example of a fastening tab is shown in U.S. patent application Ser. No. 421,640 filed Apr. 13, 1995 by Zehner et al, titled "Multi-Attachment Fastening System" the disclosure of which is hereby incorporated by reference in its entirety, to the extent such disclosure is consistent (not contradictory) with the subject matter disclosed herein.

Fastening tabs 20, 22 can be permanently secured to rear portion 14 of absorbent article 8 by, for example, ultrasonic bonding, adhesives, stitching, or other conventional and known methods of securement.

As representatively shown in FIGS. 1 and 2, bodyside liner 24 and outer cover 26 generally are coextensive and have length and width dimensions larger than the dimensions of absorbent pad 38. Thus bodyside liner 24 is generally superimposed over the entirety of the surface of outer cover 26, thereby defining the periphery of absorbent article 8. Absorbent pad 38 is disposed between outer cover 26 and bodyside liner 24 inboard of the periphery of absorbent article 8.

Bodyside liner 24 includes first skin-facing surface 58 which is compliant, soft-feeling, and non-irritating to the wearer's skin. Further, bodyside liner 24 must be sufficiently porous to be permeable to aqueous liquids, enabling such liquid to penetrate and pass through its thickness.

A suitable bodyside liner 24 may be manufactured from a wide selection of web materials. Such materials include porous foams, reticulated foams, apertured plastic films, woven and/or nonwoven natural fibers, synthetic fibers, a combination of natural and synthetic fibers, various woven and nonwoven fabrics such as meltblown or spunbonded webs of polyolefin fibers, or bonded-carded-webs composed of natural and/or synthetic fibers.

Bodyside liner 24 may be composed of a substantially hydrophobic and, therefore, substantially nonwettable material, with the hydrophobic material preferably being treated with a surfactant or otherwise processed to impart a desired level of nydrophilicity, and corresponding wettability.

In some embodiments of the invention, bodyside liner 24 is extensible, preferably resiliently extensible, in at least one direction. "Resiliently extensible" means a material that retracts nearly to its original length or width upon release of an extending force. For example, a bodyside liner that is extended 200% from its original length, thus reaching an extended length 3 times as long as the original length, and that retracts upon release of the stress, to 150% of its original length is considered resiliently extensible since a 75% return from the total amount of extension is a substantial retraction from the extended dimension.

An exemplary material for bodyside liner 24 is a nonwoven, spunbonded polypropylene fabric. See U.S. Pat. No. 5,226,992 to Morman et al, hereby incorporated by reference in its entirety, to the extent it is consistent with the disclosure herein, for teaching various materials from which bodyside liner 24 can advantageously be formed. The fabric can be creped or necked such that it is extensible in at least one of, or both of, the longitudinal direction "L" and the cross direction "C".

Bodyside liner 24 may comprise a multiplicity of components, layers, or partial layers, which correspond to any of the materials disclosed herein, as well as to others known in the art. The fabric can be treated with a selected amount of surfactant, such as about 0.28% Trition X-102 surfactant available from Rohm and Haas Corp. of Philadelphia, Pa. The surfactant can be applied by any conventional means such as spraying, printing, brush coating or the like.

In yet another embodiment of the present invention, bodyside liner 24 can comprise a stretch-bonded laminate having appropriate resilient elasticity and width to create overall surface contact between absorbent article 8 and the body of a user.

A stretch-bonded laminate comprises at least a two-layered composite in which one layer is a gatherable layer and the other layer a stretchable layer. The stretchable and gatherable layers are joined together when the stretchable layer is in a stretched condition so that, upon relaxing the composite of the joined layers, the gatherable layer is gathered.

The stretchable layer can be a film of stretchable material, such as a layer of styrene ethylene butylene styrene copolymer or other elastomeric polymer, or a plurality of optionally spaced strands of a stretchable material such as latex. Other materials having similar properties may also be provided integral with or attached to bodyside liner 24. Such materials should not interfere with the soft texture of bodyside liner 24 against the skin of the wearer.

Bodyside liner 24 preferably has an extensibility of at least about 30%, preferably at least about 100%, more preferably at least about 200%, in the cross-direction "C". In some embodiments, bodyside liner 24 additionally can have similar extensibility in longitudinal direction "L". In other embodiments, bodyside liner 24 can be extensible only in longitudinal direction "L". For example, bodyside liner can have an extensibility of at least about 30% in longitudinal direction "L".

Outer cover 26 preferably comprises a first material extending over and about substantially the entirety of the overall area of the absorbent article 8, and capable of being extended in at least the cross-direction "C". Such materials include knitted and loosely woven fabrics, bonded carded webs, spunbonded webs and meltblown webs. A meltblown web typically includes meltblown microfibers. The material may also have multiple layers such as, for example, multiple spunbonded layers and/or meltblown layers. The material may be made of polymers such as, for example, polyolefins. Exemplary polyolefins include polypropylene, polyethylene, ethylene copolymers and propylene copolymers. See U.S. Pat. No. 5,226,992 to Morman et al., hereby incorporated by reference in its entirety to the extent it is consistent (not contradictory) herewith, for teaching various materials which can be used to form outer cover 26. A preferred material for outer cover layer 26 can comprise an extensible film laminated to a necked nonwoven spunbonded material.

Alternative constructions of outer cover 26 may include a woven or non-woven fibrous web layer which has been totally or partially constructed or treated to impart desired levels of liquid impermeability to selected regions thereof, such as regions that are adjacent or proximate absorbent pad 38. Optionally, in some embodiments, an additional outer layer may overlie outer cover 26.

Outer cover 26 may optionally be composed of microporous, breathable material that enables vapors to escape from the absorbent article while preventing liquid exudates from passing through. For example, a suitable microporous film is a material known as PMP-1, which is available from Mitsui Toatsu Chemicals, Inc. a company having offices in Tokyo, Japan; or polyolefin film known as XKO-8044 and available from 3M Company of Minneapolis, Minn.

In another embodiment of the invention, outer cover 26 can be a nonwoven, spunbonded polypropylene fabric. The fabric can be creped or necked such that it is extensible in at least one of the "L" and "C" directions or in both the longitudinal direction "L" and the cross direction "C". Outer cover 26 can have an extensibility of at least about 30%, preferably at least about 100%, more preferably at least about 200%, in the cross-direction "C". In some embodiments, outer cover 26 additionally can have similar extensibility in longitudinal direction "L". For example, outer cover 26 can have an extensibility of at least about 30% in longitudinal direction "L".

Other materials having other advantageous characteristics are also useful as outer cover 26. For example, outer cover 26 can comprise a stretch-bonded laminate. Methods of making such materials are known to those skilled in the art.

Preferably both bodyside liner 24 and outer cover 26 are extensible materials. Such extensibility should enable both layers to be extended in the same direction. At least one of bodyside liner 24 and outer cover 26 preferably is resiliently extensible, i.e. retractable to at least about 75% of the amount of extension upon release of the extending force. In such embodiments, at least one of bodyside liner 24 and outer cover 26 can return absorbent article 8 to substantially its original size and shape (e.g. at least about 75% recovery of the extension) upon release of fastening tabs 20, 22 or other such extending restraints. In such an instance, the element that is merely extensible (e.g. no retractability forces) can follow the retractable liner/cover (element) to the restoration size upon release. In other embodiments, both bodyside liner 24 and outer cover 26 can be resiliently extensible, and thus can and do assist each other in returning absorbent article 8 to substantially its earlier relaxed size and shape upon release of fastening tabs 20, 22.

Leg elastics 28 may be formed from separate materials which are attached to outer cover 26 and/or bodyside liner 24. Materials suitable for forming the leg elastics include LYCRA® strands, ribbons, or one or more layers of a polymeric and/or elastomeric material that may be adhered to absorbent article 8, thus forming leg elastics 28, while in a stretched or extended position. Leg elastics 28 provide limited extensibility of the absorbent article in longitudinal direction "L", from and to a relaxed condition. Alternatively, the material forming leg elastic 28 can be attached, in a relaxed condition, to absorbent article 8 while the article is pleated, such that elastic constrictive forces are imparted to at least crotch portion 18 of absorbent article 8 when the leg elastic is elongated along the length of the absorbent article.

In embodiments where outer cover 26 and/or bodyside liner 24 are formed from materials stretchable in at least longitudinal direction "L", extensible leg elastics 28 may not need to be provided for absorbent article 8.

Opposing left and right spaced containment flaps 30, 32 extend longitudinally along the length of absorbent article 8 inwardly of respective side edges 34, 36 of the absorbent article. In such embodiments as in FIGS. 1 and 2, containment flaps 30, 32 are typically secured to bodyside liner 24. Dashed lines 56 indicate where the entire surfaces of containment flaps 30, 32 facing bodyside liner 24 are secured to the bodyside liner outwardly from crotch portion 18. Inwardly from dashed lines 56, containment flaps 30, 32 are secured to bodyside liner 24 only at the bottom surface of the containment flap contacting the bodyside liner, and thus can stand up or otherwise open to receive and restrain exudates.

Exemplary containment flaps are set forth in U.S. Pat. No. 4,704,116 issued Nov. 3, 1987 to K. Enloe, the disclosure of which is hereby incorporated by reference in its entirety to the extent that it is consistent (not contradictory) herewith.

Waist elastics (not shown) generally extend about the waist of absorbent article 8. Front waist elastics and rear waist elastics (not shown) generally comprise strands, ribbons or one or more layers of a polymeric and/or elastomeric material which can be adhered or otherwise mounted in absorbent article 8 while the elastic is in a stretched condition. Waist elastics can comprise one or more individual strands of elastomeric material, preferably in a spatially separated, generally parallel arrangement.

In some embodiments comprising cross-direction extensible outer covers 26 and/or cross-direction extensible bodyside liners 24, waist elastics can be omitted. Extensible bodyside liner 24 and/or extensible outer cover 26 can thus obviate the need for waist elastics while retaining the appropriate stretch function at the waist elements.

Absorbent pad 38 may be manufactured in a wide variety of sizes and shapes (for example, rectangular, trapezoidal, T-shape, I-shape, hourglass shape, etc.) and from a wide variety of materials. The size, and absorbent capacity, of absorbent pad 38 should be compatible with the size of the intended wearer and the anticipated liquid loading expected to be imparted by the intended use of the absorbent pad.

Absorbent pad 38 contains absorbent core 44 enveloped by first layer 40 and second barrier layer 42. Adhesive 46 preferably comprises cold adhesive applied to first layer 40 and/or second barrier 42 at least outwardly of the outer perimeter of absorbent core 44. Other Known adhesives or bonding techniques may be utilized in place of cold adhesive to secure first surface 48 of first layer 40 to first surface 52 of second barrier layer 42.

First layer 40 typically comprises a single-ply, low porosity creped wadding tissue or the like. Other materials can also function as first layer 40 provided the proper porosity and other characteristics are present. First layer 40 generally comprises a substantially non-extensible material. An exemplary first layer 40 comprises a tissue having a basis weight of 20 grams per square meter, a porosity of approximately 90 cubic feet per minute per foot squared, and dry strength of about 500 grams.

Second barrier layer 42 typically comprises a deformable material, such as a barrier tissue or an extensible material. Thus, second barrier layer 42 provides a barrier to superabsorbent material migrating from absorbent core 44 toward bodyside liner 24. An exemplary second barrier layer 42 comprises a conventional barrier tissue having a porosity of approximately 400 cubic feet per minute per foot squared, and dry strength of about 730 grams.

For the purposes of the present invention, the porosity value of any of the components can be determined by ASTM Method D 737-75 "Standard Test Method for Air Permeability of Textile Fabrics", dated Jun. 30, 1975 (reapproved 1980). The method is conducted on a single sheet of sample material. A permeability testing apparatus of the type suitable for use with this method is a high pressure differential air permeability machine, such as available from Frazier Precision Instrument Company located in Gaithersburg, Md.

Third layer 68 generally has a width at least as great as the width of first layer 40. Third layer 68 also typically has a length at least as great as the length of first layer 40. Thus, over the width and length of third layer 68, the third layer can ensure no securement of first layer 40 to outer cover 26 in the central portion of absorbent article 8, namely over absorbent pad 38. The width and length of third layer 68 preferably are greater than the width and length of first layer 40 to ensure no securement of first layer 40 to outer cover 26. Therefore, third layer 68 overlies the entirety of first layer 40.

Third layer 68 can comprise a material similar to the material used for first layer 40. In some embodiments third layer 68 comprises a substantially non-extensible layer of material, such as a non-extensible tissue. In other embodiments, layer 68 is extensible. Exemplary extensible materials for use in layer 68 can be any such materials which are recited herein as usable for outer cover 26 or bodyside liner 24.

Third layer 68 comprises a material that prevents adhesive 66 from migrating or otherwise passing through the entire thickness of the third layer, or otherwise prevents adhesive from adhering to layer 40. Various materials, capable of preventing adhesive 66 from passing through layer 68 enough to at least partially bond or otherwise tack layer 68 to layer 40, can be utilized.

Other materials having suitable characteristics may also be utilized for layers 40, 42, 68. Each of layers 40, 42, 68 can be made from multiple layers of various materials secured to each other.

Absorbent core 44 suitably comprises a matrix of hydrophilic fibers, such as a web or matt of cellulosic fluff, preferably in combination with a high-absorbency material commonly known as superabsorbent material. In a preferred embodiment, absorbent core 44 comprises a mixture of superabsorbent hydrogel-forming material and wood pulp fluff. In place of the wood pulp fluff, one may use synthetic, polymeric, meltblown fibers or meltblown or other synthetic fibers in combination with natural fibers. The superabsorbent material may be substantially homogeneously mixed with the hydrophilic fibers or may be otherwise combined into the absorbent core.

Alternatively, absorbent core 44 may comprise a laminate of fibrous webs and superabsorbent material or other suitable means of maintaining a superabsorbent material in a localized area.

The high-absorbency material in absorbent core 44 can be selected from natural, synthetic and modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains. covalent bonds, ionic complexes and associations, hydrophilic associations such as hydrogen bonding, and hydrophobic associations or Van der Waals forces.

Bodyside liner 24 is secured to outer cover 26 about at least an outer perimeter of absorbent pad 38. Typically, such securement is provided by adhesive 66. As shown in FIG. 3, adhesive 66 can comprise laterally spaced arrays of swirls of adhesive applied along longitudinal direction "L" across substantially the entirety of second surface 64 of outer cover 26. Adhesive 66 can also comprise overlapping swirl patterns of adhesive. Other patterns of adhesive are also contemplated. As described earlier, adhesive 66 secures bodyside liner 24 and outer cover 26 along side edges 34, 36. Adhesive 66 can also secure second surface 72 of third layer 68 to inner surface 64 of outer cover 26 at longitudinal sections thereof as indicated by the cross-section view of FIG. 2.

In instances where bodyside liner 24 and outer cover 26 are extensible in both cross direction "C" and longitudinal direction "L", adhesive 66 can comprise other patterns which may not include solid lines of adhesive in the longitudinal direction. For example, adhesive 66 can comprise an angled pattern of adhesives or spaced unconnected areas of adhesive applied by e.g. intermittent operation of adhesive applicators or by printing rolls. Such patterns prevent or limit adhesive 66 from "locking up" stretch of outer cover 26 in longitudinal direction "L" or cross direction "C". As used herein, "locking up" means an adhesive or glue pattern which prevents or substantially inhibits an extensible material from extending the amount and/or direction designed because the adhesive creates one or more controlling bonds at least a surface of the extensible material.

Surge layer 74 generally is located between second layer 42 and bodyside liner 24. Surge layer 74 assists in spread of exudates over a substantial portion of absorbent pad 38. Thus surge layer 74 assists absorbent pad 38 in absorbing a sudden large amount of urine or other body exudates. First surface 76 of surge layer 74 is in surface-to-surface contact with second surface 54 of barrier layer 42 and second surface 78 of the surge layer is in surface-to-surface contact with second surface 60 of bodyside liner 24.

Surge layer 74 can comprise materials set forth in U.S. Pat. No. 5,486,166 issued Jan. 23, 1996 to C. Ellis and D. Bishop, entitled, "Fibrous Nonwoven Web Surge Layer for Personal Care Absorbent Articles and the Like"; and U.S. Pat. No. 5,490,846 issued Feb. 13, 1996 to C. Ellis and R. Everett, entitled, "Improved Surge Management Fibrous Nonwoven Web for Personal Care Absorbent Articles and the Like"; the disclosures of which are herein incorporated by reference to the extent the disclosures are consistent (not contradictory) with the information disclosed herein. Further, other surge layer materials known in the art can also be utilized.

Optionally, a line of adhesive 80A extending in the longitudinal direction "L" can be disposed between surge layer 78 and absorbent pad 38. Such a line of adhesive prevents absorbent pad 38 from shifting laterally a significant distance, while enabling bodyside liner 24 to extend, at least in the cross-direction "C". Such an arrangement ensures absorbent pad 38 remains centered in absorbent article 8.

During manufacture of absorbent article 8, layer 68 effectively prevents adhesive 66 from bonding second surface 50 of layer 40 to first surface 70 of third layer 68. Second inner surface 64 of outer cover 26 is bonded to surface 72 of third layer 68 by adhesive 66. Thus third layer 68 effectively shields first layer 40 from adhering action of adhesive 66, i.e. third layer 68 is effectively free from adhesive bonding to first layer 40. Outer cover 26 is unsecured with respect to first layer 40 at least at portions overlying absorbent pad 38.

In preferred operation, bodyside liner 24 and outer cover 26 are generally extensible in the same directions. During placement of absorbent article 8 on a wearer, or at any other substantial cross-direction stretching of the absorbent article, bodyside liner 24 and outer cover 26 both extend, and third layer 68 tears or stretches. The tearing or stretching of layer 68 avoids transfer, of the stress associated with the stretching, to layer 40, layer 42, or absorbent core 44. Thus, the tearing or stretching of third layer 68 avoids damage to layer 40, and to absorbent pad 38, and accordingly avoids subsequent release of superabsorbent material from the absorbent pad.

In some absorbent articles of the invention, bodyside liner 24 and outer cover 26 are both extensible in cross-direction "C". In other absorbent articles of the invention, bodyside liner 24 and outer cover 26 are both extensible in longitudinal direction "L".

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An absorbent article including a rear portion, a front portion, and a crotch portion connecting said rear portion and said front portion, said absorbent article having a cross direction extending across said absorbent article and a longitudinal direction extending through said front, crotch, and rear portions, said absorbent article comprising:

an absorbent core including a superabsorbent material therewithin, wherein said absorbent core has an outer perimeter, a first side, and a second side;

a first layer of material having a first surface and a second surface which opposes said first surface of said first layer, wherein said first surface of said first layer is disposed adjacent to said first side of said absorbent core;

a third layer of material having a first surface and second surface which opposes said first surface of said third layer, wherein said third layer is made of a deformable material, and said first surface of said third layer is disposed in surface-to-surface relationship with said second surface of said first layer;

an outer cover made of an extensible material and having a cover perimeter, a first surface which is an outer surface, and a second surface which is an inner surface opposing said first surface of said outer cover, wherein said second surface of said third layer is disposed in surface-to-surface relationship with said second surface of said outer cover;

a second layer having a first surface and a second surface which opposes said first surface of said second layer, wherein said first surface of said second layer is disposed adjacent to said second side of said absorbent core, and said first layer and said second layer are secured to each other outwardly of said outer perimeter of said absorbent core so said first and second layers, in combination, surround said absorbent core;

a bodyside liner having a liner perimeter, a first surface which faces skin of a body of a wearer of said absorbent article, and a second surface which opposes said first surface of said bodyside liner, wherein a portion of said second surface of said bodyside liner is disposed in surface-to-surface relationship with a portion of said second surface of said second layer, and both said liner perimeter and said cover perimeter are secured to each other to contain all of said absorbent core, said first and second layers surrounding said absorbent core, and said third layer; and a first adhesive layer disposed between said second surface of said third layer and said second surface of said outer cover, wherein said first adhesive layer secure an entirely of said second surface of said third layer to an entirety of said second surface of said outer cover such that said third layer any one of deforms and tears during extension of said outer cover without any one of a harmful effect and a significant loading on said first layer, and said first layer assists in retaining said superabsorbent material of said absorbent core.

2. The absorbent article as in claim 1, wherein said third layer effectively shields said first layer from adhering action of said first adhesive.

3. The absorbent article as in claim 1, wherein said first layer is comprised of a tissue.

4. The absorbent article as in claim 1, wherein said third layer is comprised of a tissue.

5. The absorbent article as in claim 1, wherein said third layer has a width at least as great as a width of said first layer.

6. The absorbent article as in claim 1, wherein said third layer covers an entirety of said first layer.

7. The absorbent article as in claim 1, wherein said outer cover can be deformed without deforming each of said first and second layers together surrounding said absorbent core.

8. The absorbent article as in claim 7, wherein said absorbent core, said first layer, and said second layer, in combination, comprise an absorbent pad.

9. The absorbent article as in claim 8, wherein said first layer and said second layer are adhesively secured to each other outwardly of said outer perimeter of said absorbent core with a second adhesive.

10. The absorbent article as in claim 7, wherein said bodyside liner is deformable without deforming each of said first and second layers together surrounding said absorbent core.

11. The absorbent article as in claim 10, wherein at least one of said bodyside liner and said outer cover is comprised of a resiliently extensible material.

12. The absorbent article as in claim 10, wherein each of said bodyside liner and said outer cover are resiliently extensible, and each of said bodyside liner and said outer cover have substantially equal resilient extensibilities in each of said longitudinal direction and said cross direction.

13. The absorbent article as in claim 10, wherein each of said bodyside liner and said extensible outer cover are extensible in at least said cross-direction.

14. The absorbent article as in claim 1, wherein said outer cover is comprised of a neck bonded laminate.

15. The absorbent article as in claim 1, further comprising first and second containment flaps.

16. The absorbent article as in claim 1, wherein said absorbent article is devoid of separate waist elastic elements, and said absorbent article is resiliently stretchable in said cross-direction.

17. The absorbent article as in claim 1, further comprising leg elastics disposed at least in said crotch portion of said absorbent article, said leg elastics providing extensibility and retractability, of said absorbent article in said longitudinal direction.

18. The absorbent article as in claim 1, wherein said first adhesive is comprised of a pattern having an array of swirls.

19. The absorbent article as in claim 1, wherein said absorbent article is effectively free from adhesive bonding between said first layer and said third layer.

20. The absorbent article as in claim 1, wherein said third layer tears during extension of said outer cover with no harmful effect on said first layer.

21. The absorbent article as in claim 1, wherein said third layer stretches during extension of said outer cover with no harmful effect on said first layer.

22. An absorbent article including a rear portion, a front portion, and a crotch portion connecting said rear portion and said front portion, said absorbent article having a cross direction extending across said absorbent article and a longitudinal direction extending through said front, crotch, and rear portions, said absorbent article comprising:

an outer cover made of an extensible material and having a cover perimeter, a first surface which is an outer surface, and a second surface which is an inner surface opposing said first surface of said outer cover;

a bodyside liner having a liner perimeter, a first surface which is an outer body-contacting surface, and a second surface which is an inner surface opposing said first surface of said bodyside liner, wherein a portion of said second surface of said bodyside liner is mounted in surface-to-surface relationship to at least a portion of said second surface of said outer cover so that at least a portion of said cover perimeter is secured to at least a portion of said liner perimeter;

an absorbent pad disposed between said bodyside liner and said extensible outer cover, wherein said absorbent pad includes an absorbent core having a first side and a second side which opposes said first side, and said absorbent pad includes a first layer of material disposed between said first side of said absorbent core and said outer cover, and a second layer of material disposed between said second side of said absorbent core and said bodyside liner;

a third layer of material disposed between said first layer of material and said outer cover, wherein said third layer is made of a deformable material, said third layer has a first surface and a second surface opposing said first surface of said third layer, and said third layer is in surface-to-surface relationship with said first layer; and a first adhesive layer disposed between said outer cover and said third layer, wherein said first adhesive layer secures an entirety of said second surface of said outer cover to an entirety of said second surface of said third layer outer cover so that when said extensible material of said third layer is extended no significant loading occurs on said first layer, thereby preventing tearing of said first layer and preventing release of said superabsorbent material from said absorbent core.

23. The absorbent article as in claim 22, wherein said outer cover is comprised of a resiliently extensible material.

24. The absorbent article as in claim 22, wherein said outer cover is comprised of a neck-bonded laminate.

25. The absorbent article as in claim 22, wherein said bodyside liner is comprised of an extensible material.

26. The absorbent article as in claim 22, wherein each of said bodyside liner and said outer cover are extensible in at least said cross-direction, said third layer being designed to tear and thereby enable said outer cover to extend at least about 30 percent in said cross-direction without damaging any one of said first layer and said absorbent pad.

27. The absorbent article as in claim 26, wherein deforming of said third layer enables said outer cover to extend at least about 100 percent in said cross-direction without damaging any one of said first layer and said absorbent pad.

28. The absorbent article as in claim 26, wherein deforming of said third layer enables said outer cover to extend at least about 200 percent in said cross-direction without damaging any one of said first layer and said absorbent pad.

29. The absorbent article as in claim 26, wherein deforming of said third layer enables said outer cover to extend at least about 30 percent in said longitudinal direction without damaging any one of said first layer and said absorbent pad.

30. The absorbent article as in claim 22, wherein each of said bodyside liner and said outer cover are extensible in at least said cross-direction, said third layer being designed to stretch and thereby enable said outer cover to extend at least about 30 percent in said cross-direction without damaging any one of said first layer and said absorbent pad.

31. The absorbent article as in claim 22, wherein said first layer is comprised of a first tissue and said second layer is comprised of a second tissue.

32. The absorbent article as in claim 22, wherein said absorbent pad has an outer perimeter, and said first adhesive layer extends outwardly beyond said outer perimeter such that said first adhesive secures said cover perimeter of said outer cover to said liner perimeter of said bodyside liner.

33. The absorbent article as in claim 22, wherein said third layer effectively shields said first layer from adhering action of said first adhesive layer.

34. The absorbent article as in claim 22, wherein said third layer is comprised of a tissue.

35. The absorbent article as in claim 22, wherein said third layer has a width at least as great as a width of said first layer.

36. The absorbent article as in claim 22, wherein said third layer covers an entirety of said first layer.

37. The absorbent article as in claim 22, wherein at least one of said bodyside liner and said outer cover is comprised of a resiliently extensible material.

38. The absorbent article as in claim 37, wherein said absorbent article is free from adhesive bonding between said first and third layers.

39. An absorbent article including a rear portion, a front portion, and a crotch portion connecting said rear portion and said front portion, said absorbent article having a cross direction extending across said absorbent article and a longitudinal direction extending through said front, crotch, and rear portions, said absorbent article comprising:

an outer cover made of a extensible material and having a first surface which is an outer surface and a second surface which is an inner surface opposed to said first surface of said outer cover;

a bodyside liner having a first surface which is an outer body-contacting surface and second surface which is and inner surface opposed to said first surface of said bodyside liner, wherein said second surface of said bodyside liner is mounted in surface-to-surface relationship to at least a portion of said first surface of said outer cover;

an absorbent pad disposed between said bodyside liner and said outer cover, wherein said absorbent pad includes an absorbent core having a first side and a second side which opposes said first side, and said absorbent pad includes a first layer of material disposed between said first side of said absorbent core and said outer cover, and a second layer of material disposed between said second side of said absorbent core and said bodyside liner;

a third layer of material which is made of a deformable material and which is disposed between said first layer and said outer cover, wherein said third layer has first and second surfaces such that said first surface of said third layer is in surface-to-surface relationship with said second surface of said first layer; and a first adhesive layer disposed between said outer cover and said third layer for securing said second surface of said outer cover to said second surface of said third layer, wherein said first adhesive layer secures said second surface of said third layer to said second surface of said outer cover such that said third layer any one of deforms and tears during extension of said outer cover with no harmful effect on said first layer, and said first layer assists in retaining a superabsorbent material within said absorbent core.

* * * * *

UNITED STATES PATENT AND TRADEMARK OFFICE
CERTIFICATE OF CORRECTION

PATENT NO. : 6,049,023
DATED : April 11, 2000
INVENTOR(S) : Timothy J. Blenke et al.

It is certified that error appears in the above-identified patent and that said Letters Patent is hereby corrected as shown below:

Column 5,
Line 65, delete "nydrophilicity" and insert -- hydrophilicity -- in place therof.

Claim 39,
Line 12, after "and" insert -- a --;
Line 13, delete "and" and insert -- an -- in place thereof.

Signed and Sealed this

Twenty-fifth Day of December, 2001

Attest:

JAMES E. ROGAN
Attesting Officer   Director of the United States Patent and Trademark Office